United States Patent
Underhill et al.

(10) Patent No.: US 6,657,099 B1
(45) Date of Patent: Dec. 2, 2003

(54) SHEET FOR ALERTING A WEARER TO URINATION

(75) Inventors: Richard L. Underhill, Neenah, WI (US); Marsha M. Malone, Appleton, WI (US); Terry L. Adams, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 103 days.

(21) Appl. No.: 09/696,438

(22) Filed: Oct. 25, 2000

(51) Int. Cl.[7] ................................................. A61F 13/15
(52) U.S. Cl. ........................................ 604/361; 604/364
(58) Field of Search ................................ 604/361, 362, 604/364; 340/604

(56) References Cited

U.S. PATENT DOCUMENTS

| | | | |
|---|---|---|---|
| 3,794,024 A | * | 2/1974 | Kokx et al. .................. 604/361 |
| 4,790,836 A | * | 12/1988 | Brecher ....................... 604/359 |
| 4,834,733 A | | 5/1989 | Huntoon et al. |
| 5,468,236 A | * | 11/1995 | Everhart et al. ............. 604/361 |
| 5,649,914 A | | 7/1997 | Glaug et al. |
| 5,658,268 A | | 8/1997 | Johns et al. |
| 5,681,298 A | | 10/1997 | Brunner et al. |
| 5,702,376 A | | 12/1997 | Glaug et al. |
| 5,702,377 A | | 12/1997 | Collier, IV et al. |
| 5,728,125 A | * | 3/1998 | Salinas ........................ 604/361 |
| 5,797,892 A | | 8/1998 | Glaug et al. |
| 5,891,124 A | | 4/1999 | Nomura et al. |
| 6,407,308 B1 | * | 6/2002 | Roe et al. ................... 604/361 |
| 6,464,635 B1 | * | 10/2002 | Jimenez Cerrato et al. . 600/362 |

FOREIGN PATENT DOCUMENTS

EP    0 815 821 A2    1/1998

OTHER PUBLICATIONS

PCT/US01/42214 International Search Report from the European Patent Office dated May 23, 2002, 6 pages.

* cited by examiner

Primary Examiner—Weilun Lo
Assistant Examiner—Jacqueline F Stephens
(74) Attorney, Agent, or Firm—Senniger, Powers, Leavitt & Roedel

(57) ABSTRACT

A sheet including a substrate having on one face a multiplicity of tangible signalers for signaling the wearer on occurrence of urination. The substrate has urine-soluble matter on the face establishing a non-signaling condition of the tangible signalers. The urine-soluble matter is dissolved by the urine on urination enabling signaling by the tangible signalers.

28 Claims, 11 Drawing Sheets

SHEET FOR ALERTING A WEARER TO URINATION

BACKGROUND OF THE INVENTION

The present invention relates generally to undergarments, and more particularly to a sheet for use with absorbent undergarments for alerting a wearer to urination.

Disposable undergarments are highly absorbent and efficiently pull moisture away from the wearer to reduce skin irritation caused by prolonged exposure to wetness. However, because these undergarments are so absorbent, wearers may not realize they have urinated, particularly if they are inexperienced toddlers (i.e., children too young to recognize the meaning of body sensations associated with urination). Thus, the wearer may not recognize they failed to control urination or be aware the undergarment should be changed. Many parents believe that children must be given a signal such as feeling uncomfortable and wet to facilitate toilet training by making the child more aware that the act of urination has occurred. Further, some parents worry about the possibility of skin irritations and rashes caused by prolonged wetness against the skin caused by using less absorbent undergarments.

Some prior undergarments intended for toilet training include means for alerting a child that urination has occurred without leaving a substantial amount of wetness against the skin. One such prior undergarment includes a temperature changing element to allow the wearer to feel a change in temperature to alert them after urination has occurred. Another example includes an element which changes size after urination. Still another example has a high initial surface moisture immediately following urination but pulls moisture away from the wearer shortly thereafter.

Although there has been progress in articles for alerting a wearer to urination, there continues to be a need for articles such as toilet training aids which alert wearers that urination has occurred without allowing the skin to become wet.

SUMMARY OF THE INVENTION

Briefly, apparatus of this invention is a sheet including a substrate having on one face a multiplicity of tangible signalers for signaling the wearer on occurrence of urination. The substrate has urine-soluble matter on the face establishing a non-signaling condition of the tangible signalers. The urine-soluble matter is dissolved by the urine on urination enabling signaling by the tangible signalers.

In another aspect, the invention includes a sheet for alerting a wearer to urination.

In yet another aspect, the present invention includes a garment comprising an inner surface facing a wearer when the garment is worn. The surface has a multiplicity of tangible signalers extending therefrom for signaling the wearer on occurrence of urination. The signalers are covered by urine-soluble matter thereby establishing a non-signaling condition of the tangible signalers. The urine-soluble matter is dissolved by urine upon urination of the wearer enabling the tangible signalers to signal the wearer.

Other objects and features of the present invention will be in part apparent and in part pointed out hereinafter.

DESCRIPTION OF THE DRAWINGS

Corresponding reference characters indicate corresponding parts throughout the several views of the drawings.

DEFINITIONS

Within the context of this specification, each term or phrase below includes the following meaning or meanings:

"Disposable" refers to articles which are designed to be discarded after a limited use rather than being laundered or otherwise restored for reuse.

"Film" refers to a thermoplastic film made using a film extrusion and/or foaming process, such as a cast film or blown film extrusion process. The term includes apertured films, slit films, and other porous films which constitute liquid transfer films, as well as films which do not transfer liquid.

"Integral" or "integrally" is used to refer to various portions of a single unitary element rather than separate structures bonded to or placed with or placed near one another.

"Layer" when used in the singular can have the dual meaning of a single element or a plurality of elements.

"Nonwoven" refers to materials which are formed without the aid of a textile weaving or knitting process.

"Releasably attached" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

DETAILED DESCRIPTION OF THE PREFERRED EMBODIMENT

Figure 1:
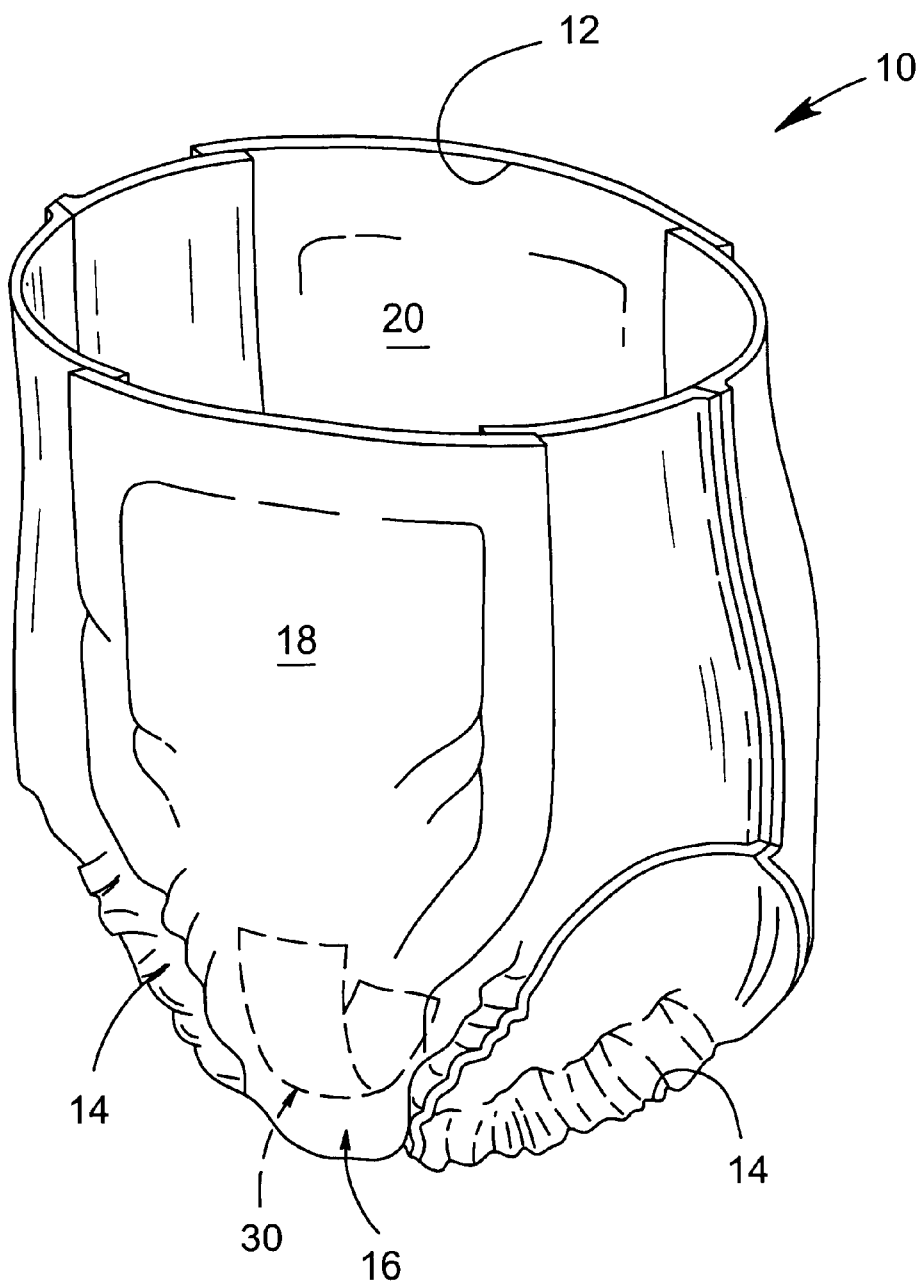
FIG. 1 is a perspective of training pants having a sheet of the present invention therein.

Referring now to the drawings and more particularly to FIG. 1, a pair of training pants is designated in its entirety by the reference numeral 10. The pants 10 have a waist opening 12 and two leg openings 14 like conventional garments. A crotch region, generally designated by 16, is located generally between the leg openings 14 and comprises that portion of the training pants which, when worn, is positioned between the legs of the wearer and covers the lower torso of the wearer. A front 18 of the training pants 10 extends generally upward from the crotch region 16 to partially cover a lower abdomen of the wearer when the training pants 10 are worn. A back 20 of the training pants 10 opposite the front 18 extends generally upward from the crotch region 16 to cover a buttocks of the wearer when the training pants are worn. By way of illustration only, various materials and methods for constructing training pants are disclosed in PCT Publication No. WO 00/37009 by Fletcher et al. published Jun. 29, 2000; U.S. Pat. No. 4,940,464 issued Jul. 10, 1990, to Van Gompel et al.; and U.S. Pat. No. 5,766,389 issued Jun. 16, 1998, to Brandon et al.; all of which are hereby incorporated by reference. A sheet of the present invention for alerting a wearer to urination is positioned generally in the crotch region 16 of the training pants 10 and is generally designated by the reference numeral 30.

Although the sheet 30 of the present invention is illustrated in FIG. 1 as being used in toilet training pants 10, the sheet may also be used in conjunction with other garments, such as underwear, diapers, diaper pants, washable or reusable absorbent garments such as woven training pants, absorbent swim pants, plastic training pants, or the like. Further, although discussed primarily in the context of toilet training for children, it should be understood that the present invention is applicable to adult personal care products such as absorbent incontinence undergarments and the like. The sheet 30 may either be part of the garment as a whole or be built directly into the garment when manufactured, or may be in the form of an insert which may be attached to any of the aforementioned garments by the consumer. If the sheet 30 is built directly into the garment or attached during manufacture, the sheet may be optionally releasably attached such that the consumer can remove the sheet if desired.

Figure 2:
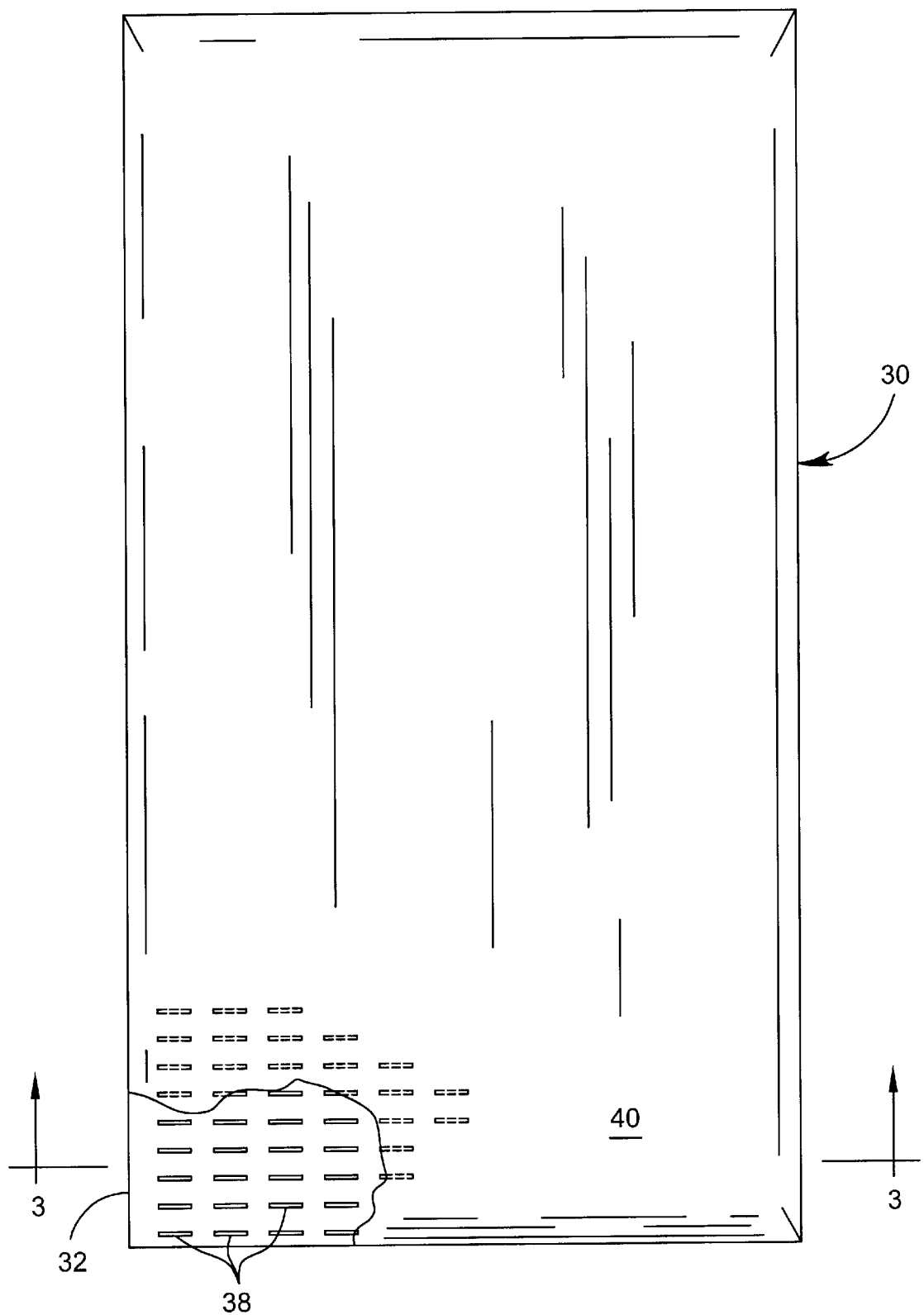
FIG. 2 is a top plan of a sheet of a first embodiment of the present invention having a layer partially broken away to show underlying features of the sheet.
Figure 3:
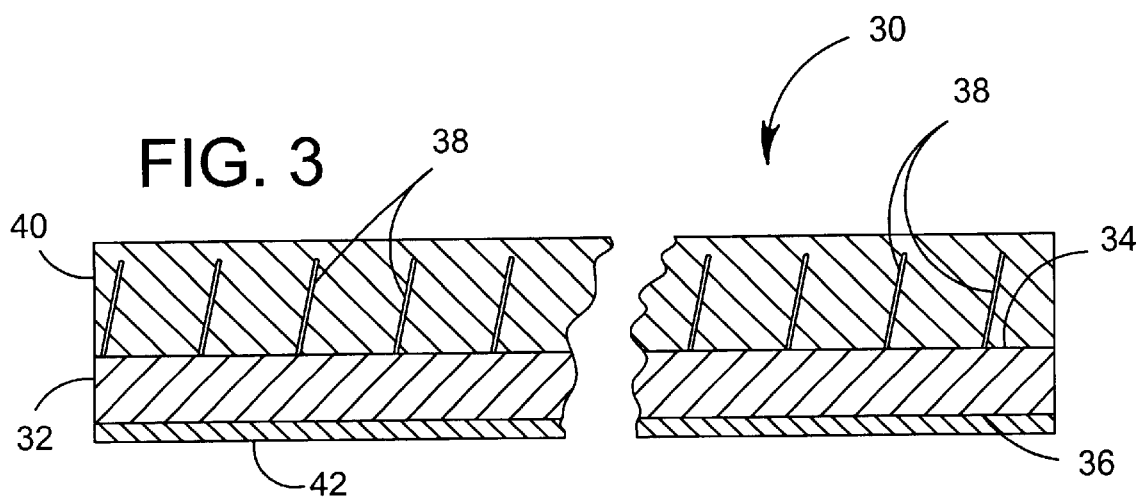
FIG. 3 is a section of the sheet of the first embodiment taken in the plane of line 3—3 of FIG. 2.

As illustrated in FIG. 2, a first embodiment of the sheet 30 of the present invention is sized and shaped for positioning in the crotch region 16 of the pants 10. Although the sheet 30 may be continuous as shown, in one embodiment (not shown), the sheet comprises an intermittent series of strips to facilitate passage of urine through the sheet to the absorbent core of the training pants. Alternatively, the sheet may have a plurality of apertures (not shown) to facilitate passage of urine through the sheet. As illustrated in FIG. 3, the sheet 30 comprises a substrate, generally designated by 32, having opposite faces 34, 36. A multiplicity of tangible signalers 38 for signaling the wearer on occurrence of urination extend from the face 34 of the substrate 32 which faces the body of the wearer when the sheet 30 is used. The substrate 32 has urine-soluble matter 40 on the face 34 to partially or completely cover the signalers 38 and to establish a non-signaling condition. The urine-soluble matter 40 is formulated to be dissolved by urine on urination of the wearer to enable the tangible signalers 38 to signal the wearer, thereby alerting the user that urination has occurred.

Although the substrate 32 may be made from other materials without departing from the scope of the present invention, in one embodiment the substrate is a polypropylene film. Polypropylene film may be desirable because it has low cost and good processability. Further, the substrate 32 may be made from other non-urine soluble materials such as other films, woven, nonwoven, porous, nonporous, airlaid, wetlaid, or foam sheets. Although the film may have other dimensions without departing from the scope of the present invention, in one embodiment the film has a thickness of between about 0.005 inches (about 0.127 mm) and about 0.25 inches (about 6.35 mm).

Although the tangible signalers 38 may be made from other materials without departing from the scope of the present invention, in one embodiment the signalers are protruding fibers integrally formed with the polypropylene film. Alternatively, it is envisioned that the fibers could be made of cellulose, polyolefin, polyamide, polyester, polyurethane, polystyrene, phenolic and epoxies without departing from the scope of the present invention. Still further, the fibers may be made of different materials than the substrate without departing from the scope of the present invention. In addition, it may be desirable that the signalers 38 be hydrophobic. Although other methods may be used to form the fibers on the film, in one embodiment the fibers are formed by a conventional calendar rolling process such as described in U.S. Pat. No. 3,594,865 issued Jul. 27, 1971, to Erb which is hereby incorporated by reference. Although the fibers may have other dimensions without departing from the scope of the present invention, in one embodiment the fibers have a length of between about 0.02 inches (about 0.5 mm) and about 0.2 inches (about 5 mm) and a diameter of between about 0.02 inches (about 0.5 mm) and about 0.2 inches (about 5 mm). Although fewer or more fibers may be used without departing from the scope of the present invention, in one embodiment the fibers cover between about 25 percent and about 75 percent of the area of the face 34 of the substrate 32.

Although the urine-soluble matter 40 may be made from other materials without departing from the scope of the present invention, in one embodiment the matter is a polyethylene oxide thermal plastic extruded over the film and fibers. Polyethylene oxide may be desirable because it has a lower melt temperature than the polypropylene film. Alternatively, it is envisioned that the urine-soluble matter 40 may be made by solution casting a polyvinyl alcohol onto the film and fibers. Still further it is envisioned that the urine-soluble matter 40 may be made from dextrines or starches without departing from the scope of the present invention. Further, the urine-soluble matter 40 may be formed from any material which is moved, dissolved and/or eliminated upon urination into the product.

Adhesive 42 may be applied to the face 36 of the substrate 32 which faces the pants 10 to attach the sheet 30 to the crotch region 16 of the pants. Although the adhesive 42 may be made of other materials without departing from the scope of the present invention, in one embodiment the adhesive is conventional hot melt adhesive or a two-sided adhesive film. Suitable hot melt or other adhesives are available from various commercial vendors such as Findley Adhesives, Inc. of Wauwatosa, Wis., USA, or National Starch and Chemical Company of Bridgewater, N.J., USA. The sheet 30 may be attached to the crotch region 16 of the pants 10 during manufacture of the garment or by the consumer.

Figure 4:
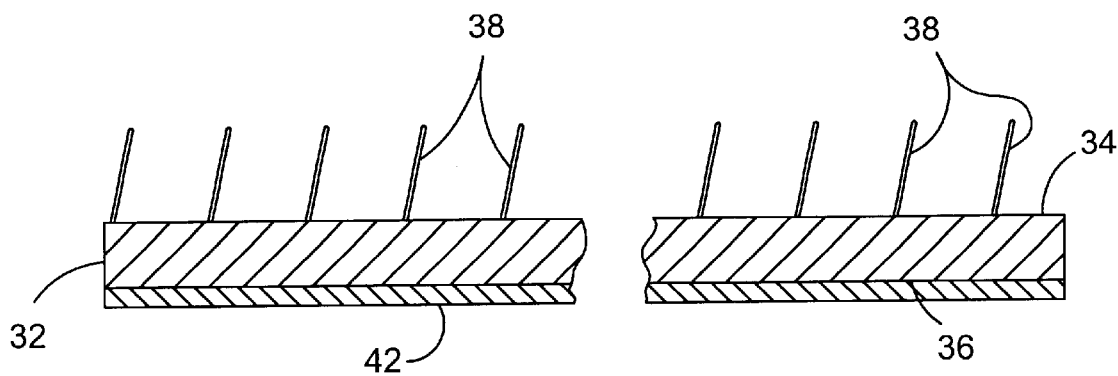
FIG. 4 is the section of the sheet of the first embodiment shown after urine-soluble matter is dissolved.

Initially, the sheet 30 has the configuration shown in FIG. 3, in which the urine-soluble matter 40 partially or completely covers the tangible signalers 38 to prevent the signalers from signaling the skin of the wearer. During and/or after urination, the urine-soluble matter 40 dissolves to expose the tangible signalers 38 as illustrated in FIG. 4. Once exposed, the signalers 38 signal the wearer to alert the wearer that he or she urinated and that his or her garment should be changed to prevent irritation of the skin.

Figure 5:
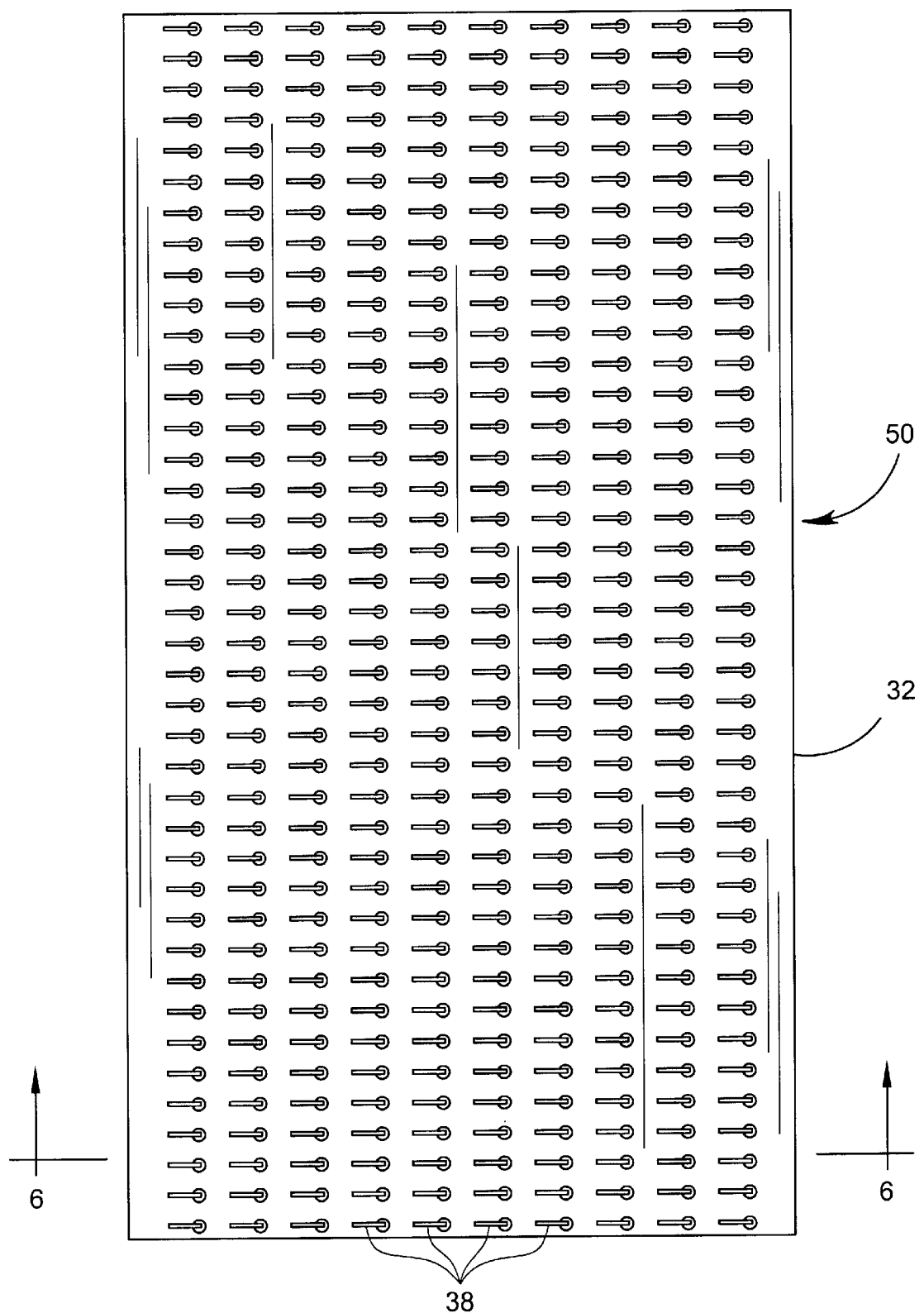
FIG. 5 is a top plan of a sheet of a second embodiment of the present invention.
Figure 6:
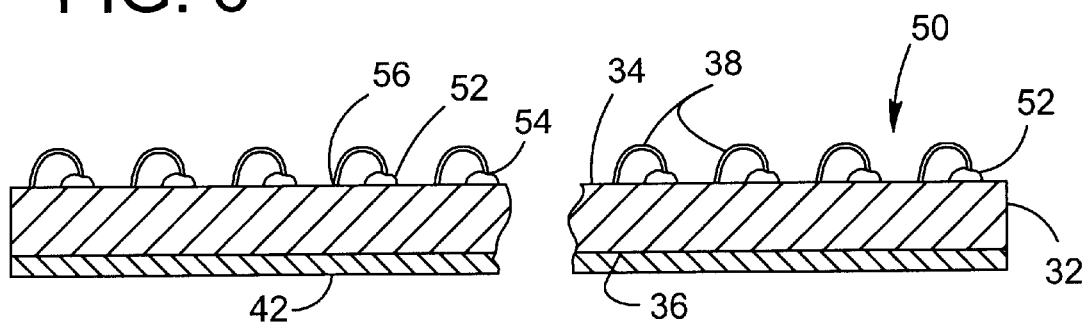
FIG. 6 is a section of the sheet of the second embodiment taken in the plane of line 6—6 of FIG. 5.
Figure 7:
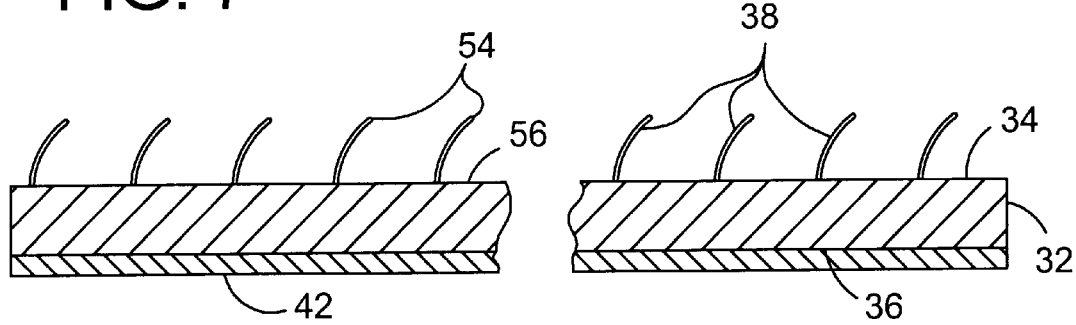
FIG. 7 is the section of the sheet of the second embodiment shown after urine-soluble matter is dissolved.

A sheet 50 of a second embodiment of the present invention is illustrated in FIGS. 5–7. The sheet 50 of the second embodiment includes a substrate, generally designated by 32, having opposite faces 34, 36 similar to the sheet 30 of the first embodiment. A multiplicity of tangible signalers 38 for signaling the wearer on occurrence of urination extend from the face 34 of the substrate 32 which faces the body of the wearer in use. Although the signalers 38 may have other configurations without departing from the scope of the present invention, in one embodiment the signalers are integrally formed fibers similar to those described above with respect to the first embodiment. The fibers may be flexibly resilient so that they can be bent over as shown in FIG. 6. Urine-soluble matter 52 is applied to an end 54 of the signalers 38 opposite an end 56 attached to the face 34. Although the matter 52 may be applied in other configurations without departing from the scope of the present invention, in one embodiment the matter is applied in spots so that one spot is positioned at the end 54 of each signaler 38. The matter 52 holds the end 54 of the signalers 38 against the face 34 to establish a non-signaling condition and to prevent the ends 54 of the signalers from signaling the skin of the wearer. During and/or after urination, the matter 52 dissolves to permit the signalers to spring away from the face 34 of the substrate 32 and stand up as shown in FIG. 7 so the ends signal the wearer to signal the wearer that urination has occurred and that the garment 10 should be changed.

Figure 8:
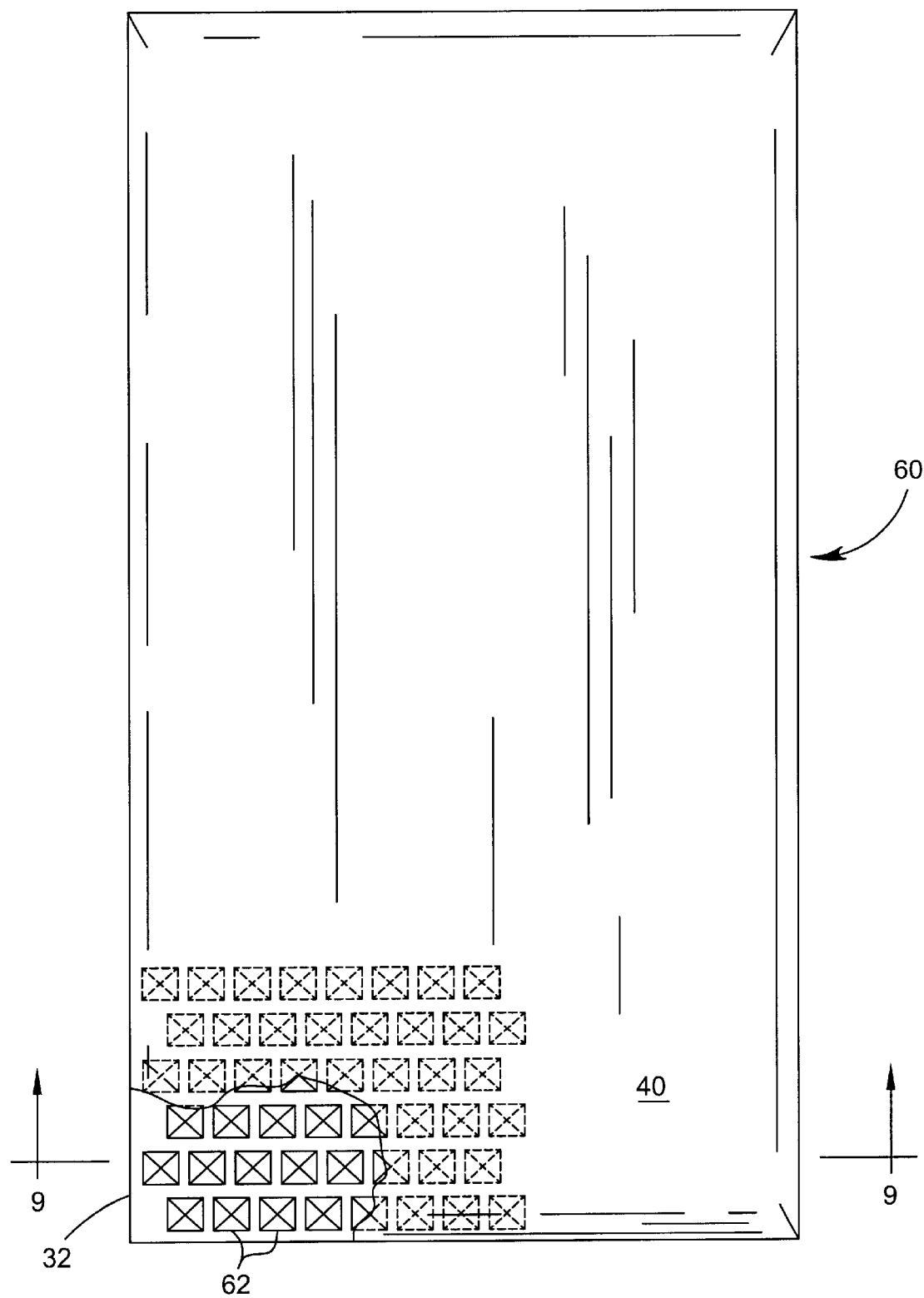
FIG. 8 is a top plan of a sheet of a third embodiment of the present invention having a layer partially broken away to show underlying features of the sheet.
Figure 9:
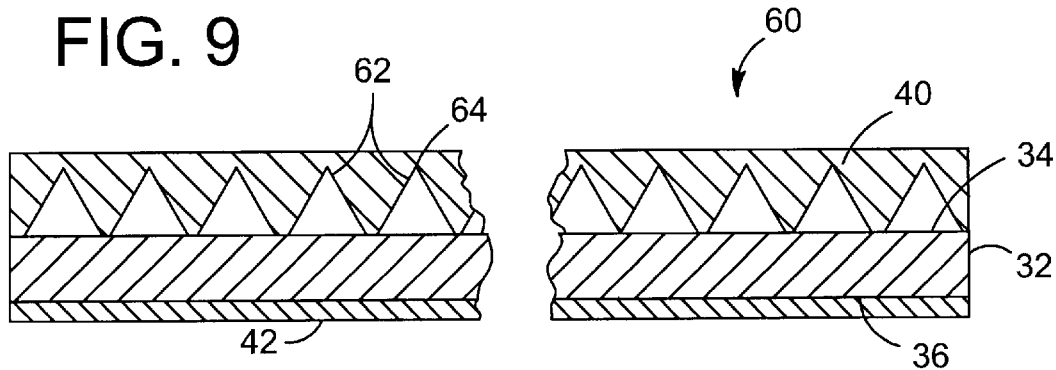
FIG. 9 is a section of the sheet of the third embodiment taken in the plane of line 9—9 of FIG. 8.
Figure 10:
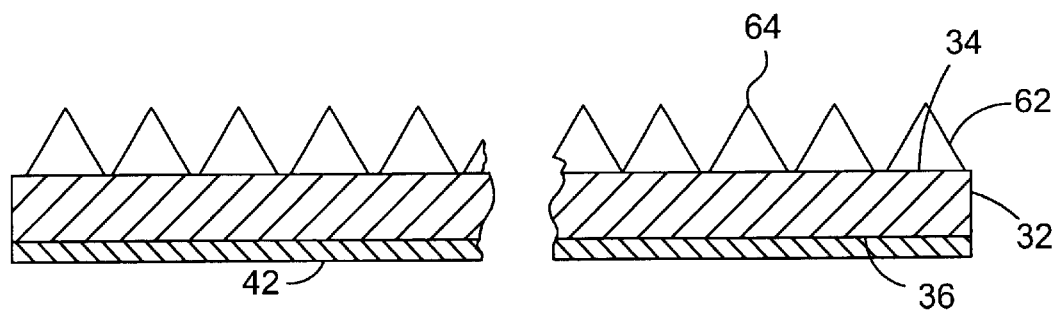
FIG. 10 is the section of the sheet of the third embodiment shown after urine-soluble matter is dissolved.

A sheet 60 of a third embodiment of the present invention is illustrated in FIGS. 8–10. The sheet 60 of the third embodiment includes a substrate 32 having opposite faces 34, 36. A multiplicity of tangible signalers 62 for signaling the wearer on occurrence of urination extend from the face 34 of the substrate 32 which faces the body of the wearer in use. Unlike the signalers of the first and second embodiments, the signalers 62 of the third embodiment are a multiplicity of projections such as pyramids having rough tips 64 formed by calendar rolling the substrate 32. Although the projections of the described embodiment are pyramids, those skilled in the art will appreciate that the projections may have other shapes without departing from the scope of the present invention. Urine-soluble matter 40 similar to that used in the first embodiment is applied over the signalers 62. The matter 40 partially or completely covers the signalers 62 to establish a non-signaling condition in which the tips 64 of the signalers are covered to prevent them from contacting the skin of the wearer. After urination, the matter 40 dissolves as illustrated in FIG. 10 to permit the tips 64 of the signalers 62 to contact the skin of the wearer to signal the wearer that urination has occurred and that the garment 10 should be changed.

Figure 11:
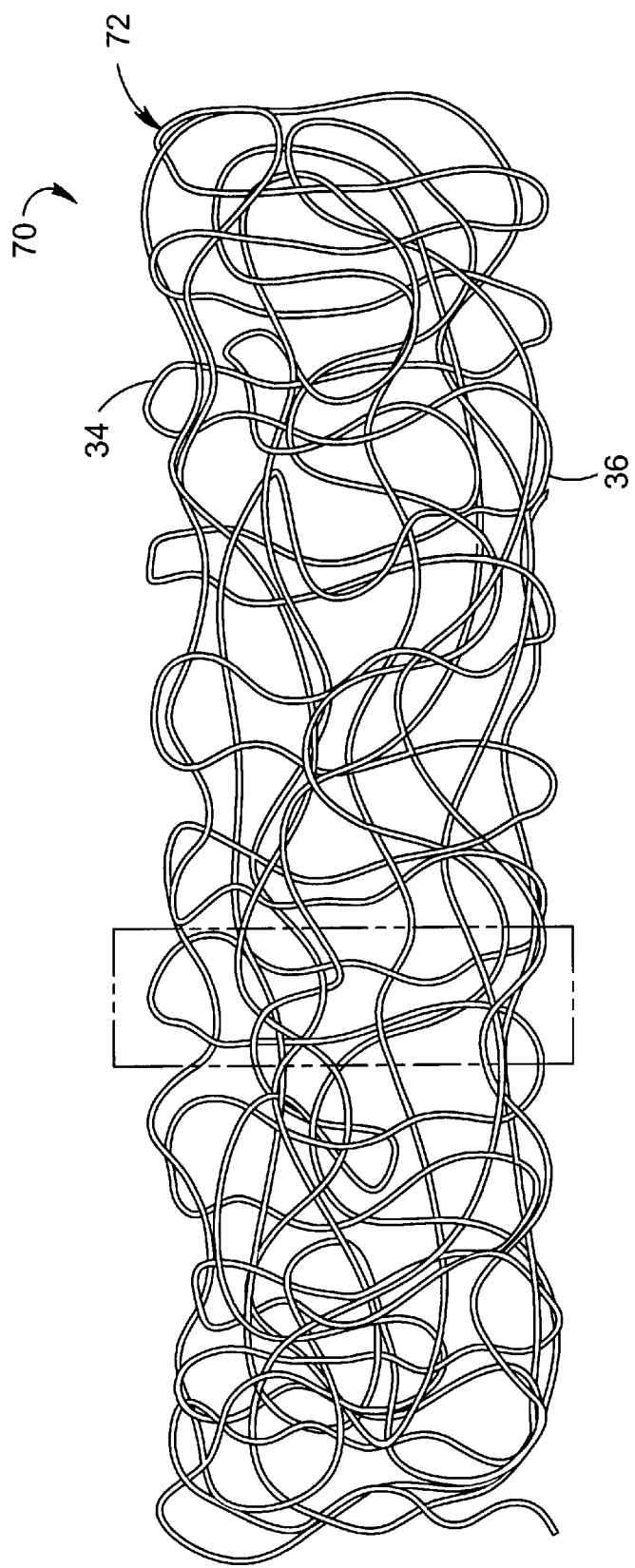
FIG. 11 is a section of a sheet of a fourth embodiment.
Figure 12:
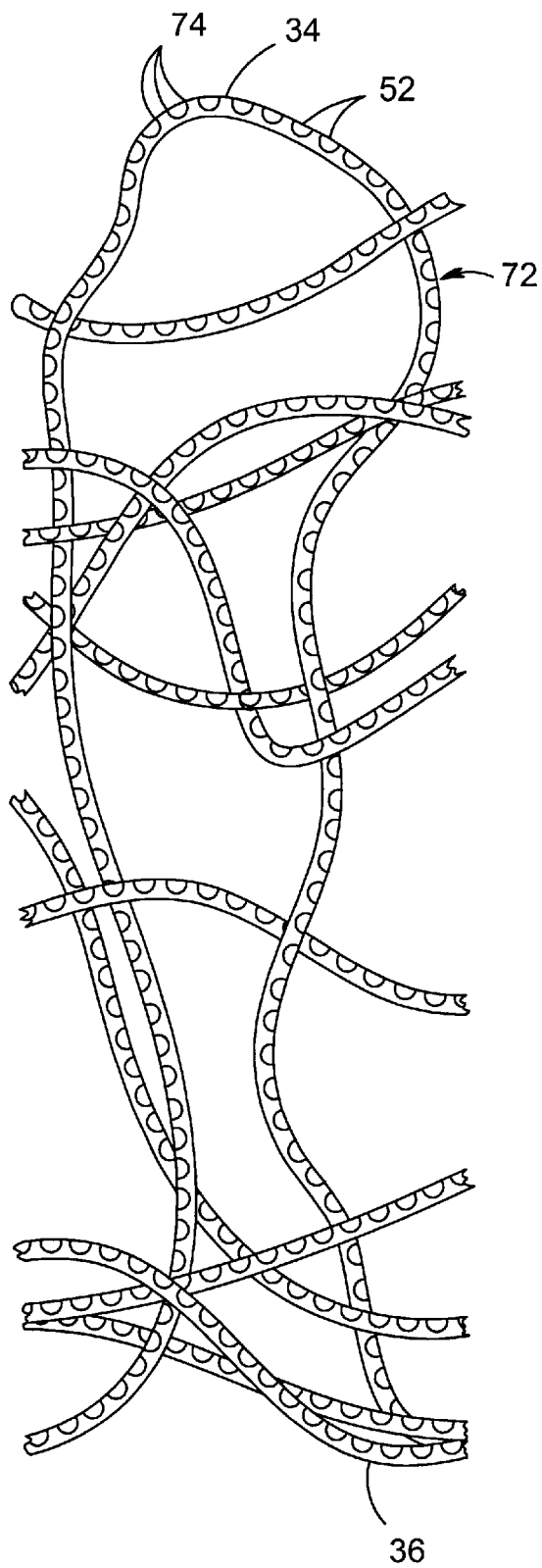
FIG. 12 is a detail of the section of the sheet of the fourth embodiment.

A sheet 70 of a fourth embodiment of the present invention is illustrated in FIGS. 11 and 12. The sheet 70 of the fourth embodiment includes a substrate, generally designated by 72, having opposite faces 34, 36. Although the substrate 72 may have other configurations without departing from the scope of the present invention, in one embodiment the substrate 72 is formed from an extruded fiber having a rough surface. Although the fiber may have other deniers without departing from the scope of the present invention, in one embodiment the fiber has a denier of between about 1 and about 150. Although the resulting substrate 72 may have other weights without departing from the scope of the present invention, in one embodiment the substrate has a weight of between about 0.3 ounces per square yard (about 10 grams per square meter) and about 10 ounces per square yard (about 340 grams per square meter). As illustrated in FIG. 12, the substrate 72 is made from an extruded fiber having a rough textured surface so the face 34 of the substrate 72 which faces the body of the wearer has a multiplicity of signalers 74 caused by the rough surfaces of the fibers. Urine-soluble matter 52 is applied to the substrate 72 to fill in the surface discontinuities of the fiber to present a smooth surface to the user prior to urination. After urination, the matter 52 dissolves to expose the rough surfaces of the signalers 74 to signal the wearer that urination has occurred and that the garment 10 should be changed.

Figure 13:
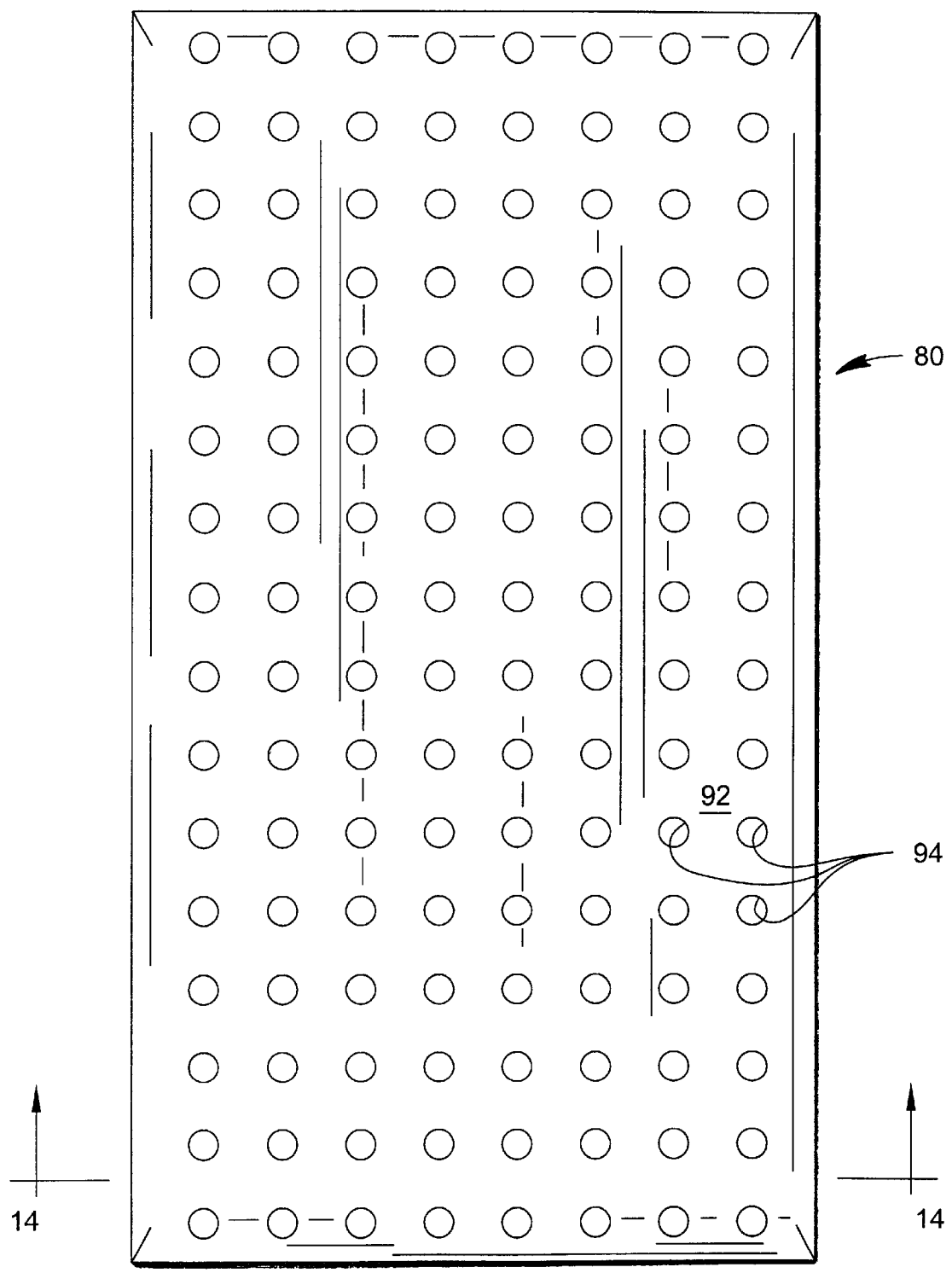
FIG. 13 is a top plan of a sheet of a fifth embodiment of the present invention.
Figure 14:
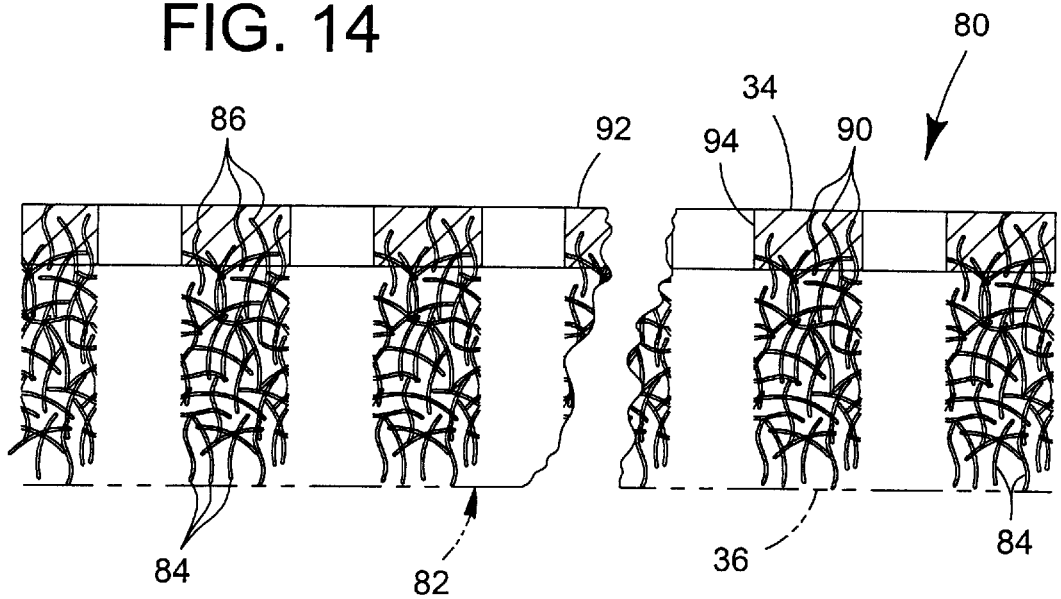
FIG. 14 is a section of the sheet of the fifth embodiment taken in the plane of line 14–14 of FIG. 13.
Figure 15:
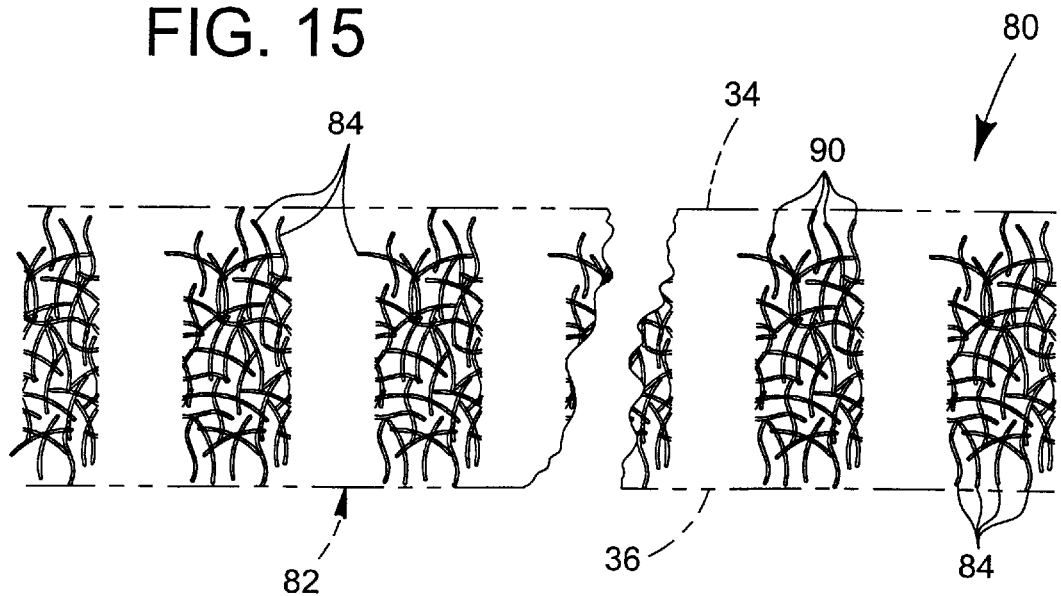
FIG. 15 is the section of the sheet of the fifth embodiment shown after urine-soluble matter is dissolved.

A sheet 80 of a fifth embodiment of the present invention is illustrated in FIGS. 13, 14 and 15. The sheet 80 of the fifth embodiment includes a substrate, generally designated by 82, having opposite faces 34, 36. Although the substrate 82 may have other configurations without departing from the scope of the present invention, in one embodiment the substrate 82 is an airlaid nonwoven web formed from staple fibers 84. Although the fibers 84 may have other deniers without departing from the scope of the present invention, in one embodiment the fibers have a denier of between about 1 and about 75. Further, although the fibers 84 may have other lengths without departing from the scope of the present invention, in one embodiment the fibers have lengths between about 0.25 inch (about 6.35 mm) and about 3 inches (about 76 mm). It is envisioned that the fibers may have a substantially uniform length or have varying lengths without departing from the scope of the present invention. Although the resulting substrate 82 may have other weights without departing from the scope of the present invention, in one embodiment the substrate has a weight between about 0.3 ounces per square yard (about 10 grams per square meter) and about 180 ounces per square yard (about 6100 grams per square meter). Although the fibers 84 may be made of other materials without departing from the scope of the present invention, in one embodiment the fibers are made of polypropylene and/or polyethylene. It is envisioned that the fibers 84 may also be made of cellulose, polyamide, polyester, polyurethane, polystyrene, phenol or epoxy combined with a binding agent such as a polyolefin (e.g., polyethylene) without departing from the scope of the present invention.

As shown in FIG. 14, the fibers 84 have ends forming a multiplicity of tangible signalers 90. Urine-soluble matter 92 is applied to the substrate 82 to partially or completely cover the signalers 90 to present a smooth surface to the user prior to urination. Although the matter 92 may be made of other materials without departing from the scope of the present invention, in one embodiment the matter is a polyethylene oxide film, or a polyvinyl alcohol or starch coating. It is envisioned that it may be desirable to apply the urine-soluble matter 92 to one face 34 as illustrated in FIG. 14 to minimize weight and material cost. However, as those skilled in the art will appreciate, it is envisioned that the urine-soluble matter 92 may partially or completely fill the substrate 82 without departing from the scope of the present invention. During and/or after urination, the matter 92 dissolves, as shown in FIG. 15, to expose the staple fibers 84 to signal the wearer that urination has occurred and that the garment 10 should be changed.

As illustrated in FIG. 13, the substrate 82 includes a plurality of holes 94 to facilitate passage of urine through the sheet 80 to the absorbent core of the training pants (not shown). Although the holes 94 may be formed at other times in the process without departing from the scope of the present invention, the holes in one embodiment are formed after the substrate 82 is coated with the urine soluble matter 92. Although the holes 94 may have other dimensions without departing from the scope of the present invention, in one embodiment the holes have diameters between about 0.04 inches (about 1 mm) and about 1 inch (about 25 mm). Although the holes 94 illustrated in FIG. 13 are circular and evenly spaced, those skilled in the art will appreciate that the holes may have other shapes and be randomly spaced without departing from the scope of the present invention.

In view of the above, it will be seen that the several objects of the invention are achieved and other advantageous results attained.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A sheet comprising a substrate having on one face thereof at least one tactile signaler adapted to tactilely signal a wearer on occurrence of urination, said substrate having urine-soluble matter on said face thereof at least partially covering said tactile signaler to establish a non-signaling condition of said tactile signaler, said urine-soluble matter being dissolved by the urine on urination to uncover said tactile signaler for enabling tactile signaling by said tactile signaler.

2. A sheet for alerting a wearer to urination comprising a substrate having on one face thereof which in the use of the sheet faces the body in the crotch region at least one tactile signaler adapted to tactilely signal the wearer on occurrence of urination, said substrate having urine-soluble matter on said face thereof at least partially covering the tactile signaler for establishing a non-signaling condition of said tactile signaler, said urine-soluble matter being dissolved by the urine on urination to uncover said tactile signaler for enabling tactile signaling by said tactile signaler.

3. A sheet as set forth in claim 2 wherein said urine-soluble matter comprises polyethylene oxide.

4. A sheet as set forth in claim 2 comprising a multiplicity of said tactile signalers, and wherein the tactile signalers are fibers extending from said face of the substrate.

5. A sheet as set forth in claim 4 wherein said substrate comprises polypropylene film.

6. A sheet as set forth in claim 5 wherein said urine-soluble matter comprises polyethylene oxide.

7. A sheet as set forth in claim 4 wherein said urine-soluble matter is applied to said face of the substrate as a coating with said tactile signalers embedded therein and thereby in said non-signaling condition, said fibers being exposed for said tactile signaling on dissolving of the coating.

8. A sheet as set forth in claim 7 wherein said urine-soluble matter comprises polyethylene oxide.

9. A sheet as set forth in claim 7 wherein said substrate comprises a polypropylene film.

10. A sheet as set forth in claim 7 wherein said urine-soluble matter comprises polyethylene oxide and said substrate comprises a polypropylene film.

11. A sheet as set forth in claim 4 wherein said fibers are resilient fibers bent over with the ends thereof held on said face of the substrate by spot applications of said urine-soluble matter and thereby held in said non-signaling condition, said fibers being adapted to spring away from said face of the substrate on dissolving of the spot applications of said matter.

12. A sheet as set forth in claim 11 wherein said urine-soluble matter comprises polyethylene oxide.

13. A sheet as set forth in claim 11 wherein said substrate comprises a polypropylene film.

14. A sheet as set forth in claim 11 wherein said urine-soluble matter comprises polyethylene oxide and said substrate comprises a polypropylene film.

15. A sheet as set forth in claim 4 wherein the fibers have a textured surface and wherein said urine-soluble matter is applied to the fibers in a manner to smooth the surface, said texture being exposed for said signaling on dissolving of said urine-soluble matter.

16. A sheet as set forth in claim 15 wherein said urine-soluble matter comprises polyethylene oxide.

17. A sheet as set forth in claim 2 comprising a multiplicity of said tactile signalers, the tactile signalers comprising projections extending from said face of the substrate and said urine-soluble matter is disposed on said face of the substrate as a coating, said projections being embedded in the coating and thereby in said non-signaling condition, said projections being exposed for said tactile signaling on dissolving of the coating.

18. A sheet as set forth in claim 17 wherein said urine-soluble matter comprises polyethylene oxide.

19. A sheet as set forth in claim 17 wherein said substrate comprises a polypropylene film.

20. A sheet as set forth in claim 17 wherein said urine-soluble matter comprises polyethylene oxide and said substrate comprises a polypropylene film.

21. A sheet as set forth in claim 2 in combination with a garment, said sheet being positioned in a crotch region of the garment.

22. A sheet as set forth in claim 2 wherein the at least one tactile signaler is connected to the sheet in both the non-signaling condition and a signaling condition.

23. A sheet for alerting a wearer to urination comprising a substrate having on one face thereof which in the use of the sheet faces the wearer in a crotch region a multiplicity of tangible signalers for signaling the wearer on occurrence of urination, said tangible signalers comprising fibers extending from said face of said substrate, said substrate having urine-soluble matter on said face thereof establishing a non-signaling condition of said tangible signalers, said urine-soluble matter being dissolved by the urine on urination enabling signaling by tangible signalers.

24. A sheet as set forth in claim 23 wherein said urine-soluble matter is applied to said face of the substrate as a coating with said tangible signalers embedded therein and thereby in said non-signaling condition, said fibers being exposed for said signaling on dissolving of the coating.

25. A sheet as set forth in claim 23 wherein said fibers are resilient fibers bent over with the ends thereof held on said face of the substrate by spot applications of said urine-soluble matter and thereby held in said non-signaling condition, said fibers being adapted to spring away from said face of the substrate on dissolving of the spot applications of said matter.

26. A sheet as set forth in claim 23 wherein the fibers have a textured surface and wherein said urine-soluble matter is applied to the fibers in a manner to smooth the surface, said texture being exposed for said signaling on dissolving of said urine-soluble matter.

27. A sheet as set forth in claim 23 in combination with a garment, said sheet being positioned in a crotch region of the garment.

28. A garment comprising an inner surface facing a wearer when the garment is worn, said surface having at least one tactile signaler extending therefrom for signaling the wearer on occurrence of urination, said tactile signaler being at least partially covered by urine-soluble matter and thereby establishing a non-signaling condition of said tactile signaler, said urine-soluble matter being dissolved by urine upon urination of the wearer to uncover said tactile signaler for enabling said tactile signaler to tactilely signal the wearer.

* * * * *

UNITED STATES PATENT AND TRADEMARK OFFICE
CERTIFICATE OF CORRECTION

PATENT NO. : 6,657,099 B1
DATED : December 2, 2003
INVENTOR(S) : Underhill et al.

It is certified that error appears in the above-identified patent and that said Letters Patent is hereby corrected as shown below:

Column 5,
Line 24, "wearer to signal the wearer that" should read -- wearer that --.

Signed and Sealed this

Fourth Day of May, 2004

JON W. DUDAS
*Acting Director of the United States Patent and Trademark Office*